United States Patent
DeLuca et al.

(10) Patent No.: US 6,291,444 B1
(45) Date of Patent: Sep. 18, 2001

(54) TREATMENT OF T-CELL IMMUNODEFICIENCIES WITH VITAMIN D COMPOUNDS

(75) Inventors: Hector F. DeLuca, Deerfield, WI (US); Shouli Yang, Memphis, TN (US); Jean M. Prahl; Connie M. Smith, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/603,041

(22) Filed: Jun. 26, 2000

Related U.S. Application Data (60) Continuation-in-part of application No. 09/159,616, filed on Sep. 24, 1998, now abandoned, which is a division of application No. 08/648,898, filed on Nov. 12, 1996, now Pat. No. 5,880,114, which is a continuation-in-part of application No. 08/413,915, filed on Mar. 30, 1995, now abandoned, which is a continuation of application No. 08/078,555, filed on Aug. 10, 1993, now abandoned.

(51) Int. Cl.[7] .................................................. A61K 31/59
(52) U.S. Cl. ............................................................. 514/167
(58) Field of Search ............................................... 514/167

(56) References Cited

U.S. PATENT DOCUMENTS

| | | | |
|---|---|---|---|
| Re. 36,854 | * 9/2000 | Sestelo et al. | 514/167 |
| 4,340,604 | 7/1982 | Aoki et al. | 424/236 |
| 4,442,093 | * 4/1984 | Maeda et al. | 424/236 |
| 4,749,710 | 6/1988 | Truitt et al. | 514/167 |
| 4,997,824 | 3/1991 | Popovitzer et al. | 514/170 |
| 5,190,935 | 3/1993 | Binderup et al. | 514/167 |
| 5,206,229 | 4/1993 | Calverley et al. | 514/167 |
| 5,225,579 | 7/1993 | Tahara | 552/653 |
| 5,274,142 | 12/1993 | Posner et al. | 552/653 |
| 5,359,055 | 10/1994 | Tsuji et al. | 540/4 |
| 5,447,924 | 9/1995 | Bretting | 514/167 |

OTHER PUBLICATIONS

Abe et al, "22–Oxa–1α,25–Dihydroxyvitamin $D_3$; A New Synthetic Analogue of Vitamin D Having a Potent Immunoregulating Activity Without Inducing Hypercalcemia in Mice," Calcium Regulation and Bone Metabolism, pp. 146–151, 1990.

Product Information, Calcijex®, Abbott Laboratories, Inc., Chicago, IL, Jun. 1997, pp. 417–418.

Boyle et al, "The Response of Intestinal Calcium Transport to 25–Hydroxy and 1,25–Dihydroxy Vitamin D in Nephrectomized Rats", Endocrinology, vol. 90, No. 3, 1972, pp. 605–608.

Boyle et al, "The Biological Activity and Metabolism of 24,25–Dihydroxyvitamin $D_3$", The Journal of Biological Chemistry, vol. 248, No. 12, Jun. 25, 1973, pp. 4174–4180.

Holick et al, "1,24,25–Trihydroxyvitamin $D_3$", The Journal of Biological Chemistry, vol. 248, No. 19, Oct. 10, 1973, pp. 6691–6696.

* cited by examiner

*Primary Examiner*—Theodore J. Criares
(74) *Attorney, Agent, or Firm*—Andrus, Sceales, Starke & Sawall, LLP (57) ABSTRACT

A method for treating a T-cell immunodeficiency in a mammal by administering an amount of a vitamin D compound, such as vitamin $D_3$, its active form 1α,25-dihydroxyvitamin $D_3$ or other compounds exhibiting vitamin D-like activity, to the mammal for a sufficient period of time to improve or restore the immunity of the mammal.

17 Claims, 6 Drawing Sheets

FIG. 6b

TREATMENT OF T-CELL IMMUNODEFICIENCIES WITH VITAMIN D COMPOUNDS

CROSS REFERENCE TO RELATED APPLICATION

This application is a continuation-in-part of application Ser. No. 09/159,616 filed Sep. 24, 1998, now abandoned, which in turn is a division of application Ser. No. 08/648,898 filed Nov. 12, 1996, now U.S. Pat. No. 5,880,114, which in turn is a continuation-in-part of application Ser. No. 08/413,915 filed Mar. 30, 1995, now abandoned, which in turn is a continuation of application Ser. No. 08/078,555 filed Aug. 10, 1993, now abandoned.

This invention was made with United States Government support awarded by the National Institutes of Health (NIH), Grant No. DK-14881. The United States Government has certain rights in this invention.

TECHNICAL FIELD

The present invention relates to cell mediated immunity functions in mammals, and more particularly to a method for improving impaired cell mediated immunity in a mammal by the administration of a vitamin D compound, such as vitamin $D_3$, its active form $1\alpha,25$-dihydroxyvitamin $D_3$ or other compounds exhibiting vitamin D-like activity, to the mammal for a sufficient period of time to improve or restore the immunity of the mammal.

BACKGROUND AND SUMMARY OF THE INVENTION

Although historically vitamin D has been associated with the regulation of mineral metabolism, it now appears certain that its functions are not confined to this system (Manolagas, Hustmyer, and Yu, (1989) Proc. Soc. Exp. Biol. Med. 191, 238–245). Receptors for the active form of vitamin D, i.e. 1,25–30 dihydroxyvitamin $D_3(1,25\text{-}(OH)_2D_3)$ are found in peripheral blood lymphocytes and thymus lymphocytes (Malogagas, Prowedini, and Tsoukas, (1985) Mol. Cell. Endocrinol. 43, 113–122) of rat and human origin. In vitro $1,25\text{-}(OH)_2D_3$ decreases one protein while increasing another in activated human lymphocytes (Yu, Hustmyer, Garvey, and Manolagas, C. (1991) Proc. Natl. Acad. Sci. 88, 8347–8351). Furthermore, $1,25\text{-}(OH)_2D_3$ in vitro exerts an anti-proliferative action on peripheral blood mono-nuclear cells (Manolagas, Provvedini, Murray, Tsoukas, and Deftos, (1986) J. Clin. Endocrinol. Metab. 63, 394–400), decreases—Interlukin-2 (IL-2) production by phytohemagglutinin-activated human peripheral mononuclear cells and decreases IL-1 activity in monocytes (Manolagas, (1988) in "Vitamin D: Molecular, Cellular and Clinical Endocrinology (Norman, Schaefer, Grigoleit, and Herrath, Eds.), pp. 282–290, Walter de Gruyter, Berlin, N.Y.). Inhibition of immunoglobulin synthesis by $1,25\text{-}(OH)_2D_3$ in B-lymphocytes has also been reported (Provvedini, Tsoukas, Deftos, and Manolagas, (1986) J. Immunol. 136, 2734–2740).

Although various biological functions for vitamin D compounds have been discovered, as indicated above, the role of vitamin D and other compounds having vitamin D-like activity on the immune system in mammals is poorly defined. To begin the assessment of the impact of vitamin D and other compounds having vitamin D-like activity on the immune system in vivo, the present disclosure provides a vitamin D deficiency model in mice and then studies the effect of this deficiency on cell mediated immunity. The effect of readministration of vitamin D compounds was then studied to determine whether or not any immune deficiency could be improved or restored.

Severe vitamin D deficiency has been produced in mice as evidenced by severe hypocalcemia and an absence of 25-hydroxyvitamin $D_3$ in blood. These and vitamin D-sufficient mice were sensitized with dinitrofluorobenzene (DNFB). Sensitivity to DNFB was determined by treatment of one ear with DNFB. The ratio of thickness of the treated ear to that of non-treated ear was used as an index of cell-mediated immune reaction. The incorporation of $^3$H-thymidine into DNA of the ear was also used as an index of cell-mediated immunity as was the response of thymus lymphocytes to concanavalin A.

Vitamin D deficiency markedly decreased the ear thickness ratio and $^3$H-thymidine incorporation ratio. Similarly, the incorporation of $^3$H-thymidine into DNA of Concanavalin A treated thymus lymphocytes was significantly reduced in vitamin D deficiency. These results show that in vivo vitamin D deficiency impairs cell-mediated immunity. The provision of a vitamin D-sufficient diet for 8 weeks corrected the impaired response of the immune system, while vitamin D administration for 3 weeks did not.

Thus, in accordance with the present disclosure, it has been found that lack of vitamin D in vivo impairs cell mediated immunity resulting in an immune deficiency in mammals. Additionally, it has been found that this immune deficiency in mammals may be improved dramatically by the administration of vitamin D compounds such as vitamin $D_3$ and $1\alpha,25$-dihydroxyvitamin $D_3$ as well as by other compounds having vitamin D-like activity, resulting in restoration if not complete repair of the immune deficiency of the mammal.

It has thus been discovered that a vitamin D compound may be utilized to treat immunodeficiencies categorized as either acquired immunodeficiencies or inherited immunodeficiencies. Acquired immunodeficiencies include human immunodeficiency virus-1 (HIV-1) infection, Herpes virus infections, Epstein-Barr virus infections, lepromatous leprosy and diminished immune capacity resulting from skin burns in burn patients, i.e. burn-related immunodeficiency. Inherited immunodeficiencies include adenosine deaminase deficiency (ADA SCID), purine nucleotide phosphorylase deficiency (PNP SCID), severe combined immune deficiency (IL-2 receptor deficiency, i.e. X-LINKED SCID), DiGeorge syndrome (no thymus), partial DiGeorge syndrome (thymic aplasia) and Bare lymphocyte syndrome (no MHC class I or II molecules to mediate positive selection of T cells in the thymus).

The results of the vitamin D deficiency model presented herein also support the use of vitamin D compounds to treat specific T-cell immunodeficiencies. These T-cell immunodeficiencies include leucocyte adhesion deficiency, lazy-leucocyte syndrome, reticular dysgenesis, and Wiskott-Aldrich syndrome (WAS).

DISCLOSURE OF THE INVENTION

The present invention comprises a method for treating immune deficiency in a mammal which comprises administering to the mammal an amount of vitamin D compound sufficient to improve the immunity of the mammal. Preferably, the vitamin D compound is administered in an amount of from about 0.1 μg to about 2 mg per day depending upon the vitamin D compound administered. Also, the vitamin D compound is preferably administered daily to the mammal for about 3 weeks to about 8 months.

As used herein the term "vitamin D compound" encompasses compounds which control one or more of the various vitamin D-responsive processes in mammals, i.e. intestinal calcium absorption, bone mobilization, bone mineralization, and cell differentiation. Thus the vitamin D compounds encompassed by this invention include cholecalciferol and ergocalciferol and their metabolites, as well as the synthetic cholecalciferol and ergocalciferol analogs which express calcemic or cell differentiation activity. Without limiting the vitamin D compounds encompassed by the present invention, these synthetic cholecalciferol and ergocalciferol analogs comprise such categories of compounds as the 5,6-trans cholecalciferols and 5,6-trans-ergocalciferols, the fluorinated cholecalciferols, the side chain homologated cholecalciferols and side chain homologated $\Delta^{22}$-cholecalciferols, the side chain truncated cholecalciferols, the 19-nor cholecalciferols and ergocalciferols, and the 10,19-dihydrovitamin D compounds.

Structurally, the vitamin D compounds encompassed may be represented by the formula where $R^6$ and $R^7$ each represent hydrogen or taken together $R^6$ and $R^7$ represent a methylene group, $R^8$ represents hydrogen, hydroxy or a protected hydroxy, and the side chain group R in the above-shown structure, may represent any steroid side chain types. More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below where the stereochemical center (corresponding to C-20 in steroid numbering) may have the R or S configuration, (i.e. either the natural configuration about carbon 20 or the 20-epi configuration), and where Z is selected from the group consisting of Y, —OY, —$CH_2OY$, —C≡CY and —CH=CHY, where the double bond may have the cis or trans geometry, and where Y is selected from the group consisting of hydrogen, methyl, —$CR^5O$ and a radical of the structure, where m and n, independently, represent the integers from 0 to 5, where $R^1$ is selected from the group consisting of hydrogen, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from the group consisting of hydrogen, fluoro, trifluoromethyl and $C_{1-5}$-alkyl, which may be straight-chain or branched, and optionally, bear a hydroxy or protected-hydroxy substituent, and where $R^1$ and $R^2$, taken together, represent an oxo group, or an alkylidene group,=$CR^2R^3$, or the group —$(CH_2)p$—, where p is an integer from 2 to 5, and where $R^3$ and $R^4$, taken together, represent an oxo group, or the group —$(CH_2)q$—, where q is an integer from 2 to 5, and where $R^5$ represents hydrogen, hydroxy, protected hydroxy, or $C_{1-5}$-alkyl.

A "protected hydroxy" group is a hydroxy group protected by any group commonly used for the temporary or permanent protection of hydroxy functions, e.g. the silyl, alkoxyalkyl, or alkyl groups. Preferred hydroxy-protecting groups are those that are base-stable, but readily removable when desired. Suitable groups are, for example, alkylsilyl- or alkylarylsilyl groups (herein referred to simply as "silyl" groups, e.g. trimethylsilyl, triethylsilyl, dibutylmethylsilyl, diphenylmethylsilyl, phenyldimethylsilyl, diphenyl-t-butylsilyl, etc.) or alkoxyalkyl groups (e.g. methoxymethyl-, ethoxymethyl, methoxyethoxymethyl, etc., or tetrahydropyranyl, tetrahydrofuranyl groups), as well as alkyl groups from 1 to 6 carbons (e.g. methyl, ethyl, propyl, isopropyl, etc.).

Some specific examples of such compounds include vitamin D metabolites or analogs such as vitamin $D_3$, vitamin $D_2$, 1α-hydroxyvitamin $D_3$, 1α-hydroxyvitamin $D_2$, 1α,25-dihydroxyvitamin $D_3$, 1α,25-dihydroxyvitamin $D_2$, 25 hydroxyvitamin $D_3$, 25-hydroxyvitamin $D_2$, 24,24-difluoro-25 hydroxyvitamin $D_3$, 24,24-difluoro-1α, 25-dihydroxyvitamin $D_3$, 24-fluoro-25-hydroxyvitamin $D_3$, 24-fluoro-1α, 25-dihydroxyvitamin $D_3$, 2β-fluoro-25-hydroxyvitamin $D_3$, 2β-fluoro 1α-hydroxyvitamin $D_3$, 2β-fluoro-1α,25-dihydroxyvitamin $D_3$, 26,26,26,27,27,27-hexafluoro-25-hydroxyvitamin $D_3$, 26,26,26,27,27,27-hexafluoro-1α,25-dihydroxyvitamin $D_3$, 24,25-dihydroxyvitamin $D_3$, 1α,24,25-trihydroxyvitamin $D_3$, 25,26-dihydroxyvitamin $D_3$, 1α,25,26-trihydroxyvitamin $D_3$, 23,25-dihydroxyvitamin $D_3$, 23,25,26-trihydroxyvitamin $D_3$, and the corresponding 1α-hydroxylated forms, 25-hydroxyvitamin D3-26,23-lactone and its 1α-hydroxylated derivative, the side chain nor, dinor, trinor and tetranor-analogs of hydroxyvitamin $D_3$ and of 1α,25-dihydroxyvitamin $D_3$, 1α-hydroxypregnacalciferol, and its homo and dihomo derivatives, 1α,25-dihydroxy-24-epi-vitamin $D_2$, 24-homo-1,25-dihydroxyvitamin $D_3$, 24-dihomo-1,25-dihydroxyvitamin $D_3$, 24-trihomo-1,25-dihydroxyvitamin $D_3$ and the corresponding 26- or 26,27-homo, dihomo or trihomo analogs of 1α,25-dihydroxyvitamin $D_3$ as well as the corresponding 19-nor compounds of those listed above.

The present invention is further described by means of the following illustrated examples. In the examples, the following abbreviations are used: 1,25-$(OH)_2D_3$, 1,25- dihydroxyvitamin $D_3$; 25-OH-D, 25-hydroxyvitamin D; IL-2, Interlukin-2; DTH, Delayed-type hypersensitivity; DNFB, Dinitrofluorobenzene; A/O, acetone/olive oil; HBSS, Hanks' balanced salt solution; con A, concanavalin A; PHA, phytohemagglutinin; SI, stimulation Index; B1, Thiamin; B2, Riboflavin; B6, Pyridoxine; B12, cyanocobalamine; IUdR, 5-iododeoxyuridin.

MATERIALS AND METHODS

Vitamin D-deficient mice. In the first experiment, BALB/CANNHSD female mice (virus free, Harlan Sprague Dawley, Indianapolis, Ind.) in the 14th day of pregnancy were divided into three groups. The first and second groups (–D group and +D group) were fed purified vitamin D-deficient diet (–D diet, Table 1) and vitamin D-sufficient diet (+D diet), respectively. The +D diet is the same as the –D diet except vitamin $D_2$ (ergo calciferol) 5070 IU/kg (126.75 μg/kg) (National Research Council (1978) Committee on Animal Nutrition, Agriculture Board, "Nutrient Requirements of Laboratory Animals", 3rd Rev. Ed., No. 10. Natl. Acad. Sci., Washington, D.C.) is added. The purified diet (Table 1) contained 0.47% calcium and 0.3% phosphorus, and was made into gel form as follows: 25 g agar (Difco Laboratories, ifco, MI) in 1 L deionized water was autoclaved for 30 min, 1 Kg of the purified diet and 5 ml fat-soluble vitamin (A, E, and K for –D diet and A, D, E, and K for +D diet) mixture (Table 2) was added to the agar solution, mixed, poured into glass pans, solidified at room temperature, then stored at –20° C. until feeding. The third group of pregnant mice (normal group) was fed Formulab #5008 pellet diet (Purina Mills, St. Louis, Mo.) which contained 23.5% protein, 6.5% fat, 3.8% fiber, and 15,000 IU/kg vitamin A, 3,800 IU/kg vitamin D, 55,000 IU/kg vitamin E (α-tocopherol), 1% calcium, and 0.65% phosphorus. The mouse pups were weaned at age 3 weeks and were fed the same diet as their dams. The mice delivered by the dams of the first group were divided into two groups at age ten weeks: one group (–D group) was continued on the purified –D diet, and the other—group (–D+D group) was fed purified +D diet for the remaining three weeks.

In the second experiment, BALB/CANNHSD female mice were divided into two groups: –D group and +D group which were fed –D and +D diet, respectively. At the same time, they were mated with male mice. The litters of mice also were weaned at age 3 weeks and were fed the same diet as their dams for 13 weeks. Then all of the mice were supplied Formulab #5008 pellet diet for 8 weeks. The two groups of mice were called –D+P group and +D+P group, respectively.

All mice were housed in plastic cages carpeted with chips, and exposed to 12 h of yellow light and 12 h of darkness. The diets and tap water were available ad libitum throughout the course of the experiments.

Assay for serum calcium and 25-hydroxyvitamin D. Serum total calcium level was determined on 25 μl of serum in Model 4008 Calcette (Precision Systems, Natick, Mass.) or by combining 50 μl of serum with 2.95 ml of 5% $LaCl_3$ by atomic absorption spectrophotometry (Model 403, Perkin-Elmer, Norwalk, Conn.).

Serum 25-hydroxyvitamin D [25-OH-D] was measured using a 0.2 ml sample (Belsey, DeLuca, and Potts, (1974) J. Clin. Endrocrinol. Metab. 38, 1046–1051). Binding protein used in the assay was obtained from Holtzman rats fed a vitamin D deficient diet for more than 6 weeks. Aliquots of 10 μl serum were stored frozen at –80° C. and were diluted to 1/8,500 with phosphate buffer (50 mM, pH 7,2) for use in the assay. The samples of mouse serum were added to 10 μl $^3$H-25-OH-$D_3$ (specific activity: 160 Ci/mM, 1 Ci=37 GBq; New England Nuclear, Boston, Mass.) to monitor recovery. The samples were vortexed, incubated for 15 min at room temperature, extracted with 0.6 ml methanol, and centrifuged at 1500 rpm for 15 min. The supernatant was mixed with 0.4 ml $H_2O$, and transferred to a C18 Sep-Pak column (Waters, Millipore Corp. Milford, Mass.) (Hollis and Frank (1985) J. Steroid 343, 43–49) through a glass wool pipette filter. The columns were then rinsed successively with 4 ml of 55%, 10 ml of 70% and 20 ml of 80% methanol in $H_2O$. The last fraction was evaporated under nitrogen and redissolved in 100 gl of absolute ethanol. 20 μl were used in triplicate for competitive binding assay; an aliquot of 30 μl was counted in a liquid scintillation counter (Tri-Carb 460CD Liquid scintillation System, Packard Instrument Co., Inc.) for calculating recovery. The detection limit of this assay procedure is 3.0 ng/ml serum.

Delayed-type hypersensitivity (DTH) response. The mice aged 13 weeks were divided into two subgroups for each of the four groups (–D, –D+D, normal, and +D groups) in the first experiment and for two groups (–D+P and +D+P) aged 18 weeks in the second experiment. One subgroup was DNFB-sensitized (DNFB subgroup) and one subgroup (A/O subgroup) served as control. 10 mg/ml of Dinitrofluorobenzene (DNFB) solution in acetone/olive oil=1/1 (w/w) vehicle served as a skin contact antigen. On day 0, 50 μl and on day 7, 20 μl of DNFB solution was applied to the shaved abdominal skin for mice of DNFB sensitized subgroup. The control mice (A/O subgroup) received the vehicle at the same time (Smith, Levy, and Hayes, (1987) J. Nutr. 117, 857–865). At 7.5 days after the first sensitization, all mice were injected intraperitoneally (i.p.) with 0.2 ml saline containing 5 μCi of $^3$H-thymidine (specific activity 20 Ci/mmol, NEN, DuPont Co., Wilmington, Del.) (Eipert and Miller (1975) Immunol. Commun. 4, 361–372). On the 9th day, all mice were challenged with 10.1 of DNFB antigen solution on the dorsal side of the left ear and the same amount of vehicle solution on the right ear. One day later, the mice were sacrificed by ether. Thymus and spleen were excised and spleen was weighed. The thymus was immediately placed in ice-cold Hanks' balanced salt solution (HBSS) (Hudson and Hay (1976) Practical Immunology, P. 269–276, Blackwell Scientific Publications, Oxford, London) until use. The ear thickness was immediately measured with Yuano 1 -J micrometer (NSK Japan Micrometer) and was expressed as a thickness ratio of left to right ear. It should be emphasized that the control ear also received the acetone/olive oil vehicle solution in the DNFB-sensitized subgroup. The control mice (non sensitized subgroup) also had a DNF13 challenged ear. The DNFB sensitization position is on the abdomen, but the DNFB challenge position is on the ear.

The ear and spleen were dissolved in 1 ml solubilizer (Soluene 350, Packard Instrument Co., Inc. Downers Grove, Ill.; or TS-1 tissue solubilizer, International Research Products Inc., Elk Grove Village, Ill.) in large glass standard scintillation vials at 45° C. for 5 h. Because the solubilizers are quaternary ammonium hydroxide, the solubilized samples were acidified with 50 μl of concentrated hydrochloric acid (HCl) to eliminate strong chemiluminescence. The radioactivity of the tissue samples was counted in a liquid scintillation counter (Tri-Carb 460CD Liquid Scintillation System, Packard Instruments, Downers Grove, Ill.) with 10 ml Biosafe II scintillation fluid (International Research Products Inc., Mt. Prospect, Ill.). Disintegrations per min (DPM) of the samples were obtained through the autocorrection program, using standard quenching series samples prepared with solubilized ear or spleen tissue as quenchers and $^3$H toluene (ICN #77245, SA: 2,360,000 DPM/ml) as internal standard. The ratio of radioactivity of left ear to right ear was calculated.

Lymphocyte proliferation. After rinsing with HBSS, the thymus tissue was pressed through a stainless steel mesh in HBSS. The cell suspension was centrifuged (400×g) for 15 min. The lymphocytes were suspended in RPMI-1640 medium (Gibco, Grant Island, N.Y.) supplemented with 5% heat inactivated fetal bovine serum (FBS), 2 mM L-glutamine and antibiotics (100 μg/ml of streptomycin, 100 U/ml of penicillin). Then cells were counted and cell viability assessed by trypan blue exclusion (greater than 95%). The suspension of lymphocytes was utilized directly.

Cultures were performed in triplicate in 96 well flat bottomed microtiter plates (#25860, Corning Glass Works, Comin, N.Y.), with a seeding of 5×10$^5$ cells/well. The mitogen concanavalin A (con A, 0.5 μg/well, Sigma) was added. The mitogen dose used was previously established as optimal. The cells were incubated for 48 h at 37° C. in a humidified atmosphere containing 5% $CO_2$ and 95% air. At 18 h before harvesting, 0.5 μCi/well $^3$H-thymidine was added. The cells were harvested on glass microfiber filter strips (model 240-1, Cambridge Technology, Inc., Watertown, Mass.) and washed three times with double distilled water and one time with absolute methanol sequentially in a Harvester (Model PHD 252A. Cambridge Technology, Inc.). The radioactivity was counted in packard Model 460 CD liquid scintillation system. The stimulation Index (SI) was calculated by the following formula:

SI=(cpm of culture with mitogen—cpm of background culture)/(cpm of culture without mitogen—cpm of background culture) in which the background culture did not contain $^3$H thymidine and mitogen. When the lymphocytes were incubated, no other factors were added except for mitogen.

Statistics. The Student's t-test was used to determine significance. In the case of difference of means with unequal population variances (heterogeneity of variance), t'-test or nonparametric Wilcoxon's test was used to estimate the significance (Taylor (1991) Statistical Techniques for Data Analysis, Lewis Publishers, Inc., Chelsea, Minn. and Tate and Clelland (1957) Nonparametric and Shortcut Statistics, Interstate Printers and Publishers, Danville, Ill.).

Figure 1A:
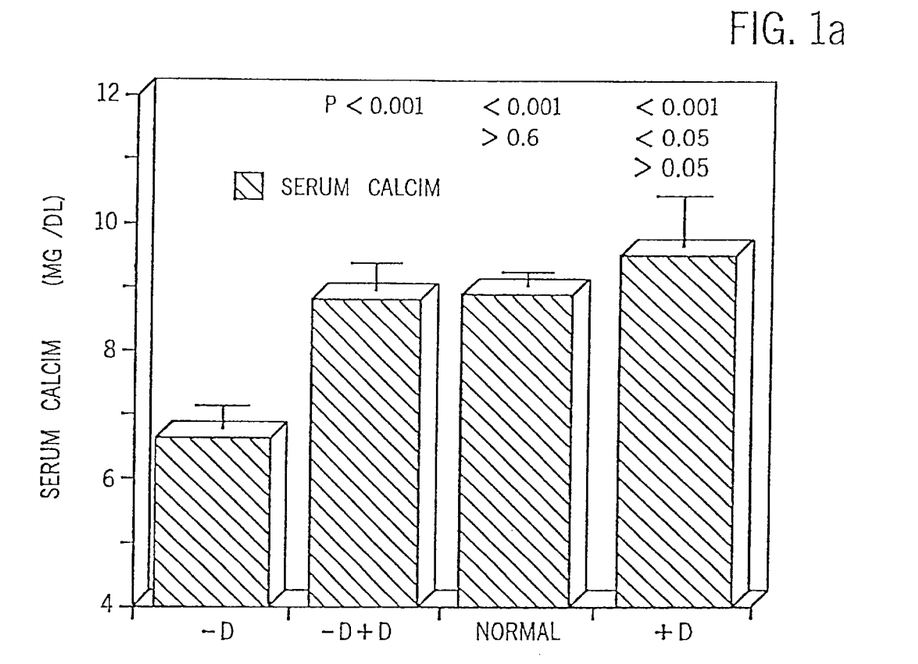
FIG. 1a is a bar graph of serum calcium concentration in mice for four groups (−D, −D+D, normal, and +D) at age 13 weeks in the first experiment.
Figure 1B:
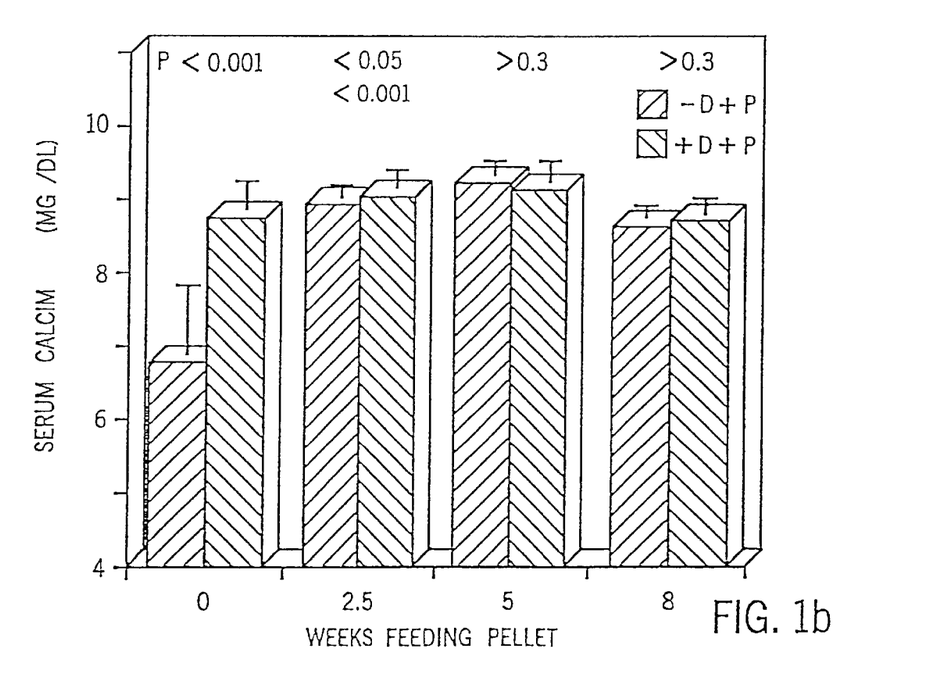
FIG. 1b is a bar graph of serum calcium concentration in mice for two groups (−D+P and +D+P) supplied a pellet diet for 8 weeks after feeding −D or +D purified diets for 13 weeks in the second experiment.

FIG. 1a shows serum calcium concentration in mice for four groups (–D, –D+D, normal and +D) at age 13 weeks in the first experiment and FIG. 1b for two groups (–D+P and +D+P) supplied Formulab #5008 pellet diet for 8 weeks after feeding –D or +D purified diets for 13 weeks. In FIG. 1a, the P values in the first row over the graph are the significances of differences between the serum calcium concentration of –D group and the group under the P value. The values in the second row (or third row) are the significances of differences between –D+D (or normal) group and the group under the P value. In FIG. 1b, the P values in the first row represent the significance of difference between –D (or –D+P) and +D (or +D+P) groups at the supplemental period under the P values. The P value in the second row represent the significance of difference between –D group at 0 week and –D+P group at 2.5 weeks feeding pellet diet.

Figure 2A:
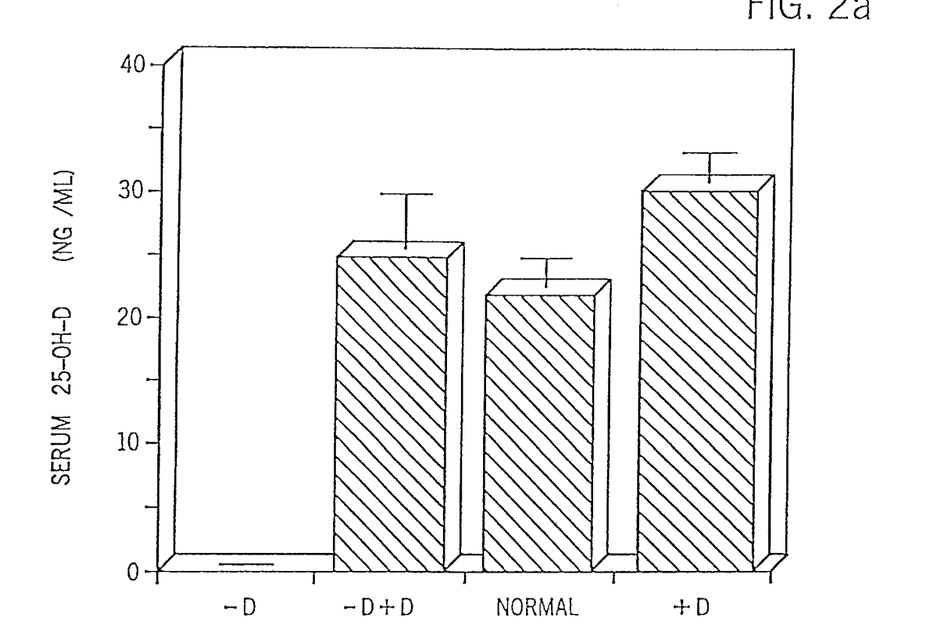
FIG. 2a is a bar graph of serum 25-hydroxyvitamin $D_3$ concentration in mice for the same four groups at 13 weeks in the first experiment.
Figure 2B:
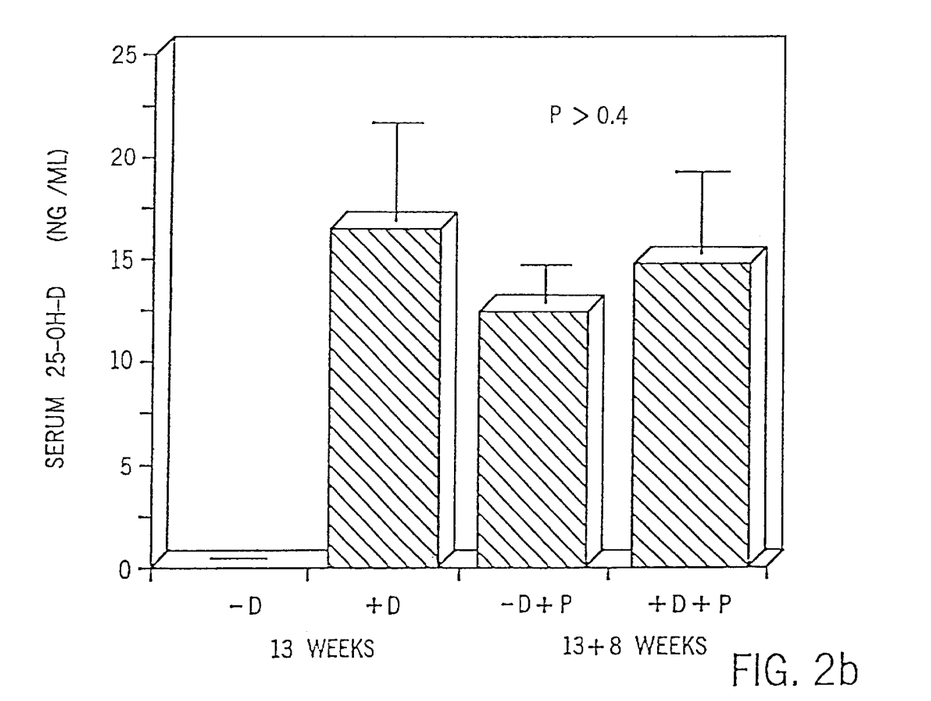
FIG. 2b is a bar graph of serum 25-hydroxyvitamin $D_3$ concentration in mice for the same two groups in the second experiment.

FIG. 2a shows serum 25-OH-D concentration of mice for four groups at 13 weeks in the first experiment and FIG. 2b for two groups (–D+P and +D+P) supplied Formulab #5008 pellet diet for 0 and 8 weeks after feeding –D or +D purified diets for 13 weeks in the second experiment. The P value in FIG. 2b is as described for FIG. 1b.

Figure 3A:
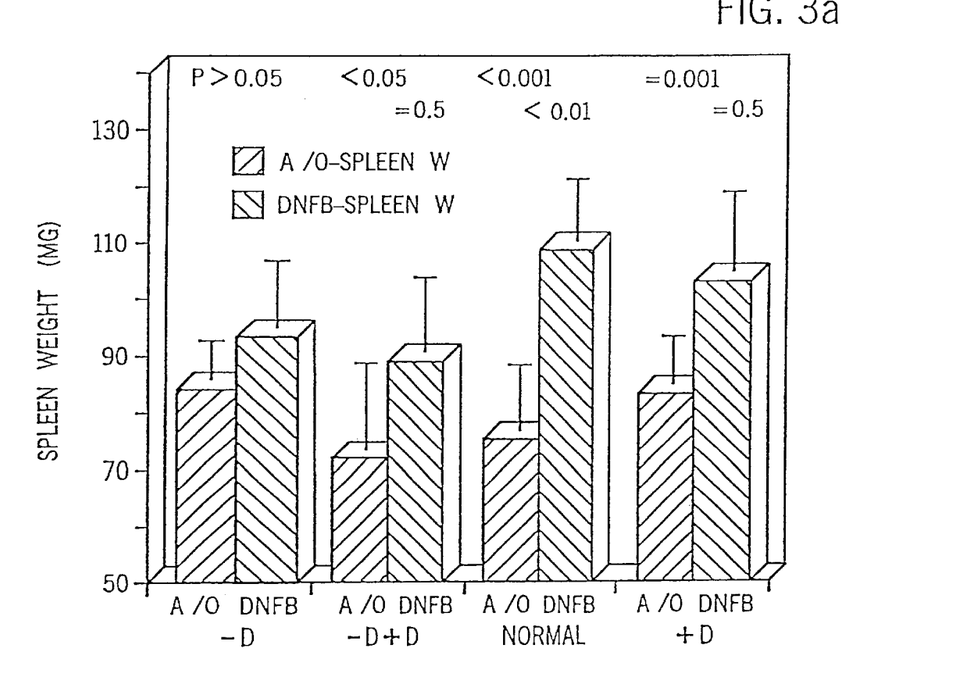
FIG. 3a is a bar graph of the effect of deficiency and supplementation with vitamin D on spleen weight of mice in the first experiment.
Figure 3B:
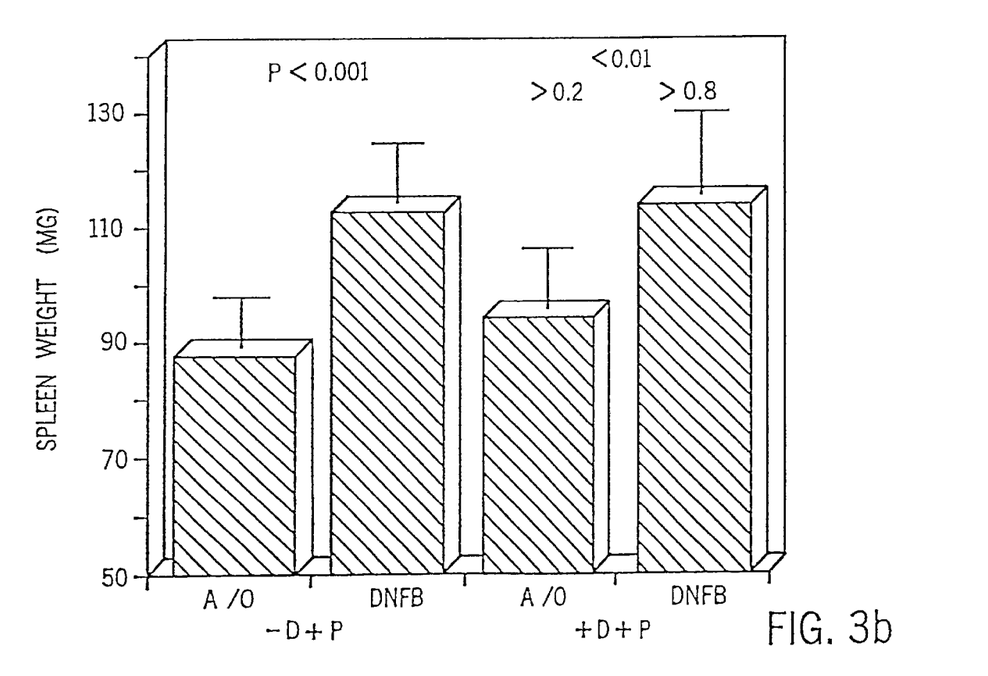
FIG. 3b is a bar graph illustrating the same effects with respect to the second experiment.

FIG. 3a shows the effect of deficiency and supplementation with vitamin D on spleen weight of mice in the first experiment while FIG. 3b shows the same effect for the second experiment. In FIG. 3a, the P values in the first row over the graph are the significance of difference of spleen weight between the DNFB sensitized subgroup and control subgroups under the P values. The P values in second row are the significances of differences between the DNFB-sensitized subgroups under the P values. In FIG. 3b the P values in the first row are as described for in the first row of FIG. 3a. The value in the second row represents the significance of difference between the subgroups of +D+P group under the P values and corresponding subgroups in –D+P group.

Figure 4A:
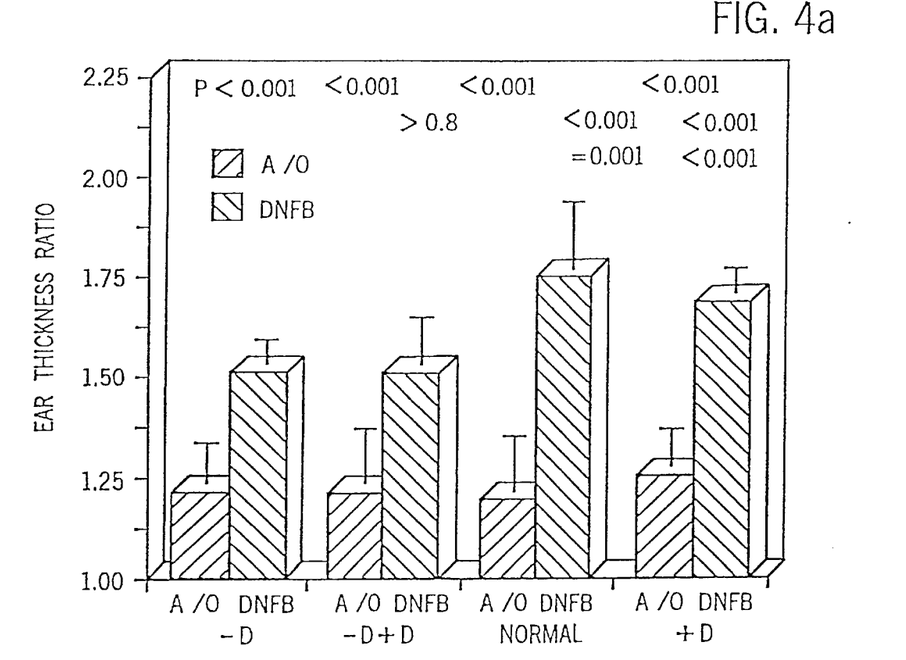
FIG. 4a is a bar graph of the ear thickness ratio of DNFB-challenged ear to control ear for mice in the first experiment.
Figure 4B:
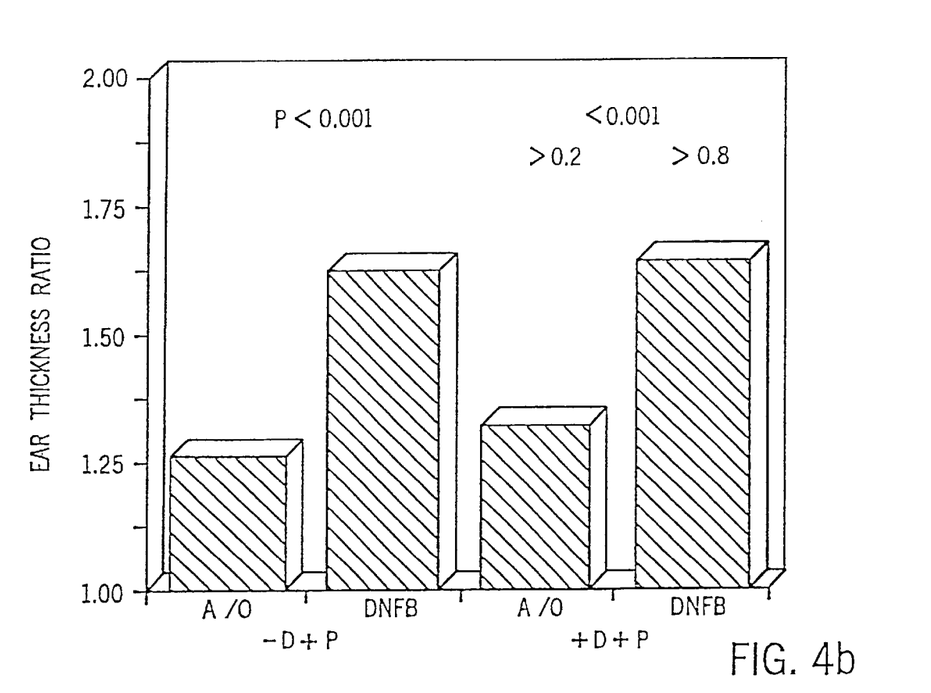
FIG. 4b is a bar graph of the same ear thickness ratio with respect to the mice in the second experiment.

FIG. 4a shows the thickness ratio of DNFB-challenged ear to control ear for mice in the first experiment while FIG. 4b shows the same ratio in the second experiment. The P values are as described for FIGS. 3a and 3b.

Figure 5A:
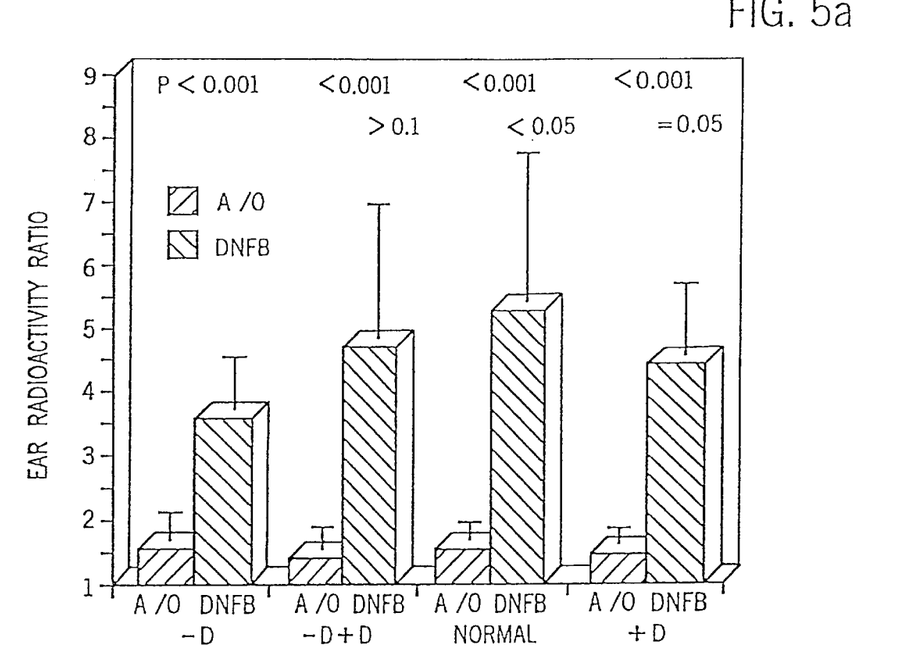
FIG. 5a is a bar graph of the ear radioactivity ratio of DNFB challenged ear to control ear for the mice in the first experiment.

FIG. 5a shows the radioactivity ratio of DNFB-challenged ear to control ear for the mice in the first experiment while FIG. 4b shows the same ratio in the second experiment. The P values are designated as in FIGS. 3a and 3b.

Figure 6A:
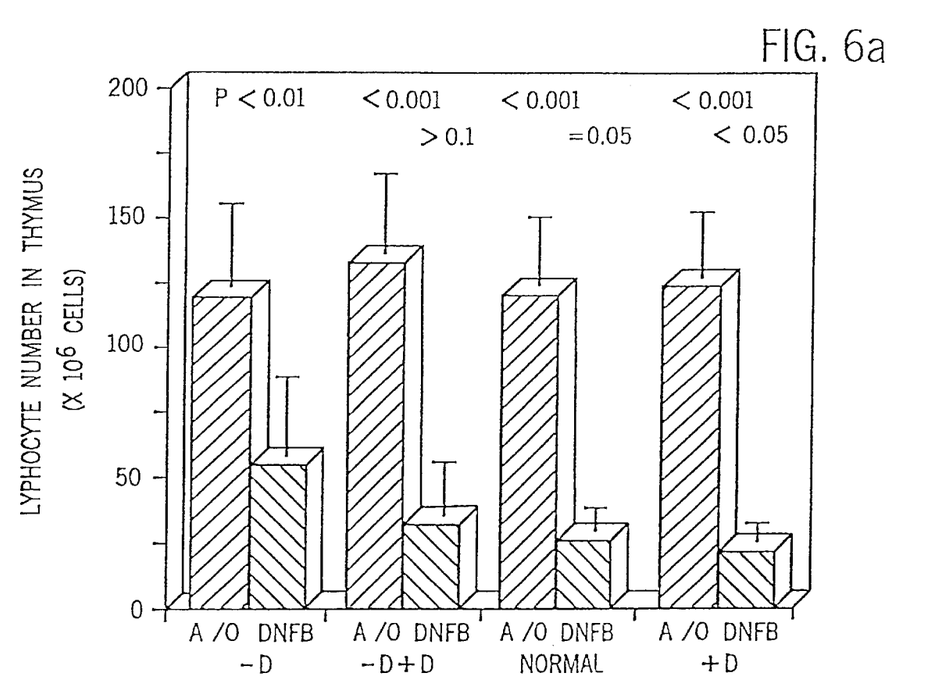
FIG. 6a is a bar graph of the comparison of lymphocyte number and thymus of the four mouse groups in the first experiment.

FIG. 6a shows the comparison of lymphocyte number in thymus among –D, –D+D, normal and +D groups in the first experiment and FIG. 4b the effect of vitamin D-deficiency on stimulation index of thymus lymphocytes in mice non-sensitized or sensitized with DNFB. The wells were seeded with 5×105 cells/well. Con A was added at 0.5 µg/well, and incubation was continued for 48 h. The cells were harvested at 18 h after $^3$H thymidine (0.5 µCi/well) was added. The P values are as described in FIG. 3a.

RESULTS

Vitamin D deficient in mice. Serum calcium concentrations of mice for four groups (−D, −D+D, normal, and +D) at age 13 weeks and for two groups (−D+P and +D+P) supplied pellet diet for 8 weeks after feeding −D or +D purified diets for 13 weeks are shown in FIGS. 1a and 1b, respectively. The mice fed the −D diet for 13 weeks had a serum calcium of 6.64±0.41 mg/dl (mean±SD, n=12; FIG. 1a). The mice fed the +D diet had a serum calcium concentration of 9.50±0.84 mg/dl (n=4), which was significantly higher than that of the −D group (p<0.001). The normal mice fed Formulab #5008 pellet showed a serum calcium concentration of 8.89±0.27 mg/dl (n=10) which was also markedly higher than that of the −D group (p<0.001), but there was no significant difference in the serum calcium concentrations of the +D groups (p>0.05). The mice that were fed −D diet for ten weeks and the +D diet for three weeks showed a serum calcium concentration of 8.81±0.45 mg/dl (n=12). It was also markedly higher than that of the −D group (P<0.001), and not significantly different from the serum calcium concentration in normal mice (p>0.6). This fact indicated that supplementation of the diet with vitamin D2 for three weeks after the feeding −D diet for ten weeks markedly increases serum calcium concentration, but its level is slightly lower than that of the +D group (p<0.05).

In the second experiment, the mice fed purified −D or +D diet for 13 weeks (age 13 weeks), the serum calcium in −D mice (6.76±0.97 mg/dl, n=12; FIG. 1b) was markedly lower than that in +D mice (8.71±0.41 mg/dl, n−10; P<0.001). By feeding these −D mice the Formulab #5008 pellet diet for 2.5 weeks, serum calcium increased significantly (8.88±0.19 mg/dl, n=18, P<0.001). However, it was also significantly lower that in the +D+P group at the same supplemental period (9.00±0.25 mg/dl, n=16; P<0.05). After 5 and 8 weeks of the pellet diet, serum calcium of−D+P group (9.18±0.23 mg/dl, n=11, and 8.56±0.20 mg/dl, n=8, respectively) was not significantly different from the +D+P group (9.07±0.35 mg/dl, n=11, and 8.66±0.19 mg/dl, n=8, respectively; both P>0.3).

The mice of the +D group in the first experiment gave serum 25-OH−D concentration of 30.9±2.6 ng/ml (n=2), and all three samples of the −D group mice gave undetectable serum 25-OH−D concentrations (<3.0 ng/ml, FIG. 2a). The concentrations for the −D+D and normal groups were 25.4±4.5 ng/ml (n=3) and 22.5 ±2.4 ng/ml (n−2), respectively. The results of serum calcium and 25-OH−D levels showed that the mice of the −D group were indeed vitamin D deficient, and that supplement of +D diet for three weeks increased markedly the serum calcium and 25-OH−D concentrations.

For the second experiment, serum 25-OH−D of four samples in −D group at 13 week were less than minimum detectable level (FIG. 2b), while +D+P group had serum 25-OH−D concentration of 16.3±4.8 ng/ml, n=4). When the mice were fed Formulab #5008 pellet diet for 8 weeks after feeding the purified diets for 13 weeks, serum 25-OH−D of −D+P group (12.2±2.1 ng/ml, n=3) was not significantly different from that of +D+P group (14.6±4.1 ng/ml; P>0.4).

These results showed that supplement of vitamin D for 8 weeks completely restored serum calcium and 25-OH−D levels in serum to normal.

There were significant differences in the spleen weights between DNFB-sensitized subgroups and control subgroups for normal and +D, and −D+D groups in the first experiment (FIG. 3a ; p<0.001, −0.001 and <0.05, respectively) and for −D+P and +D+P groups of the second experiment (FIG. 3b ; P<0.001 and <0.01, respectively), but the −D group in the first experiment was excepted (p>0.05, FIG. 3a). or normal mice, DNFB sensitization markedly increased spleen weight indicating a normal immunologic response, this response was markedly decreased in the −D mice. The spleen weight in the DNFB sensitized subgroup of the −D mice was obviously less than that in the DNFB sensitized subgroup of normal mice (P<0.01, FIG. 3a), and was nearly significantly less than that in DNFB sensitized subgroup of +D mice (P=0.05; FIG. 3a). The difference between the DNFB sensitized subgroups in −D and −D+D groups was not significant (p=0.5). This suggests that a supplement of vitamin DZ for three weeks after feeding −D diet for ten weeks did not restore the spleen immune response. The results of the second experiment showed that a supplement of vitamin D (Formulab #5008 pellet diet) for 8 weeks after feeding −D diet for 13 weeks could restore the spleen immune response; the spleen weight in DNFB sensitized subgroup of −D+P group (112.6±10.5 mg, n=10; FIG. 3b) was not significantly different from that in DNFB sensitized subgroup of +D +P group (113.8±14.9 mg, n=10; P>0.8, FIG. 3b). The difference in spleen weight in A/O control subgroups between −D+P and +D+P groups was also not significant (P>0.2).

Delayed-type hypersensitivity. FIG. 4a illustrates the thickness ratio of DNFB-challenged ear to control ear in mice fed purified diets (−D or +D) or normal pellet diet for 13 weeks in the first experiment and FIG. 4b in the mice supplied vitamin D (Formulab #5008 pellet diet) for 8 weeks after feeding−/+D purified diets for 13 weeks. First, six control subgroups possess essentially the same ear thickness ratio (1.21±0.15 to 1.32±0.10). But the ratio of ear thickness in the DNFB-sensitized subgroups were significantly higher than the ratio in the control subgroups (p<0.001) for all of six groups. This indicates that the DNFB sensitization is an excellent method for assessing delayed type hypersensitivity. Second, the ratio of ear thickness in the DNFB sensitized subgroup of −D group in the first experiment is markedly lower than that in the DNFB sensitized subgroup of the normal mice (1.55±0.07, n=11 to 1.80±0.19, n=12; p<0.001; FIG. 4a), and also of +D mice (1.73±0.008, n=12; p<0.001). These data illustrate vitamin D-deficiency significantly decreases the DTH in mice. Third, the ratio of ear thickness in the DNFB sensitized subgroup of −D+D mice (1.54±0.14, n=12) was essentially the same as that in the DNFB sensitized subgroup of −D mice (p>0.8), but it is significantly lower than that in the DNFB sensitized subgroups of normal mice (p=0.001) and of +D mice (P<0.001; FIG. 4a). These results proved that although a supplement of vitamin D for three weeks increased serum calcium and 25-OH−D concentrations to near normal levels (FIGS. 1 and 2), the DTH response had not responded. Fourth, the difference of ear thickness ratio between DNFB sensitized subgroup in −D+P group (1.62±0.12, n=10; FIG. 4b) and in +D+P group (1.64±0.17, n=10) was not significant (P>0.8). Thus, impaired DTH response found in vitamin D deficiency (13 weeks) can be corrected by providing vitamin D for 8 weeks.

Figure 5B:
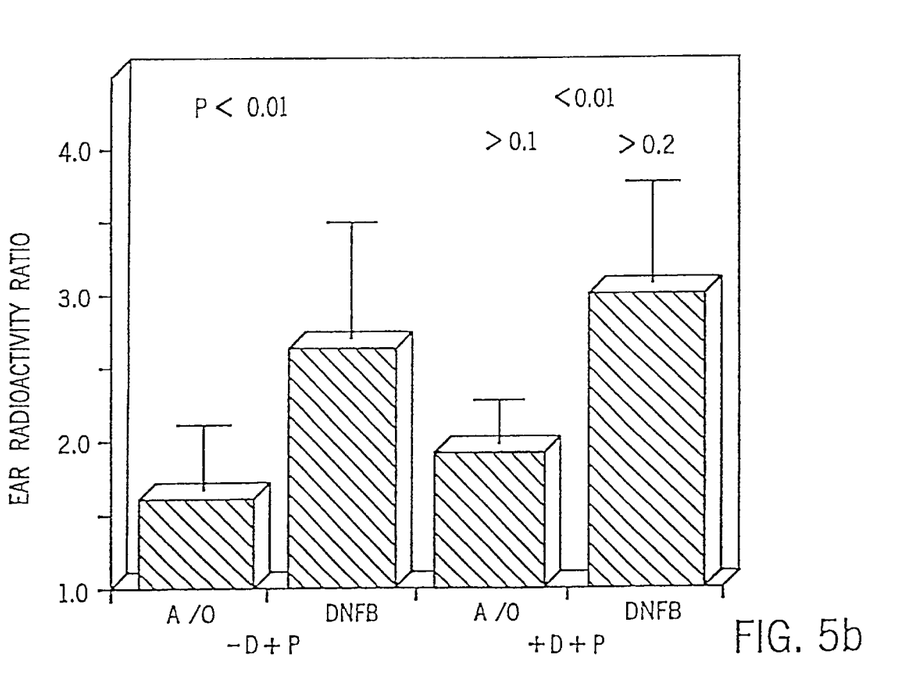
FIG. 5b is a bar graph illustrating the same ear radioactivity ratio with respect to the mice in the second experiment.

In the case of $^3$H-thymidine incorporation into mouse ears, all of the six control subgroups possess nearly the same radioactivity ratio of DNFB challenged ear to control ear (1.43±0.40 to 1.91±0.32) (FIGS. 5a and 5b). The differences in ratio of radioactivity between the DNFB sensitized subgroups and the control subgroups were highly significant for all six groups [P<0.001 for four groups in the first experiment (FIG. 5a), and P<0.01 for −D+P and +D+P groups in the second experiment (FIG. 5b)]. This demonstrates that 3H-thymidine incorporation into DNFB challenged ears in the DNFB sensitized subgroup is higher than that in the control subgroup, and also suggests that $^3$H-thymidine incorporation is a meaningful method of assessing DTH response. The radioactivity ratio of ears for DNFB sensitized subgroup in −D mice is significantly lower than that in the normal mice (p<0.05; FIG. 5a), and is nearly significantly lower than that of DNFB sensitized subgroup in +D mice (p=0.05). The difference of ear radioactivity ratio of the DNFB sensitized subgroup between −D and −D+D groups and between −D+P and +D+P groups are not significant (p>0.1, FIG. 5a and p>0.2, FIG. 5b, respectively). Thus, vitamin D for three weeks did not correct the impaired cell-mediated immunity induced by vitamin D deficiency but vitamin D for 8 weeks was able to do so.

Lymphocyte proliferation. The thymus lymphocyte number in four control subgroups of the first experiment were approximately the same (FIG. 6a). The thymus lymphocyte numbers in the DNFB-sensitized subgroups were obviously less than that in control subgroups for all four groups in the first experiment: 58±33 (n=6) to 126±35 (n=6) (p<0.1) for the −D group, 33±23 (n=6) to 139±32 (n=6) (p<0.0001) for the −D+D group, 28±10 (n=6) to 125±29 (n=6) (p<0.001) for +D groups, respectively. The difference in lymphocyte numbers between the sensitized subgroups in −D and −D+D groups was not significant (p>0.1).

Figure 6B:
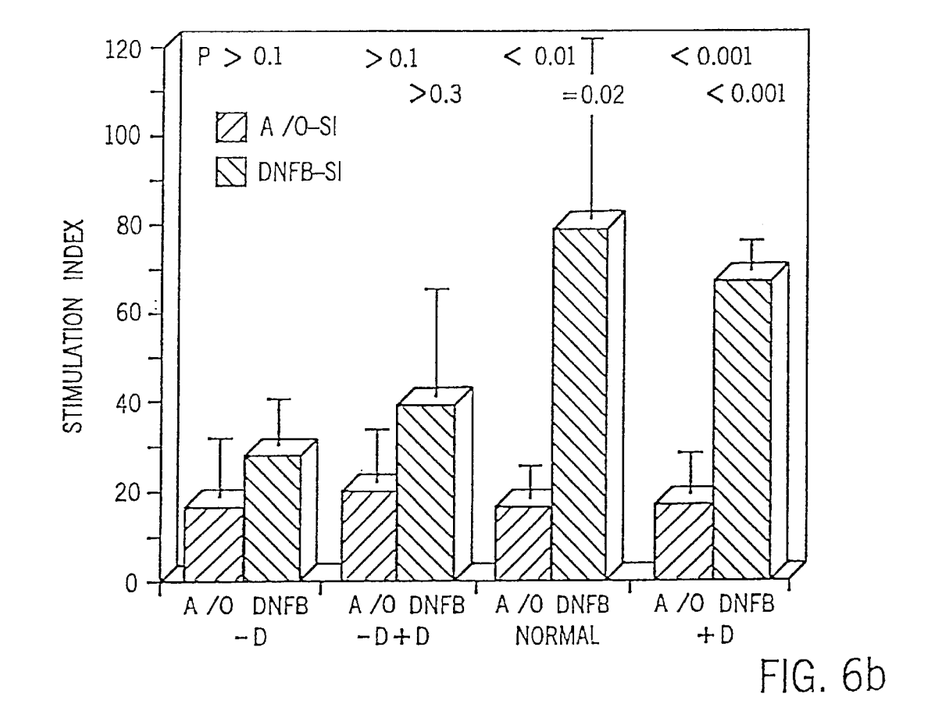
FIG. 6b is a bar graph of the effect of vitamin D deficiency on the stimulation index of thymus lymphocytes in mice non-sensitized or sensitized with DNFB for the same four mouse groups in the first experiment.

The stimulation index of thymus lymphocytes by con A (0.5 μg/well) was approximately the same for all four control groups in the first experiment (FIG. 6b). The stimulation index of the DNFB-sensitized subgroups were markedly higher than control subgroups in normal group [78.0±43.3 (n=6) to 15.9±7.7 (n=6); p<0.1], and in +D group [66.6±7.3 (n=6) to 16.3±9.4 (n=6); p<0.00], but for the −D and +D groups, the differences between SI of the DNFB-sensitized subgroup and control subgroup were not significant: 28.1±11.1 (n=6) to 17.1±12.7 (n=6); p>0.1 for −D group, and 38.7±24.8 (n=6) to 20.0±12.0 (n=6); P>0.1 for −D+D group. This shows that the −D and −D+D thymus lymphocytes had an obviously lower response to mitogen stimulation than those from +D and normal mice. The SI of DNFB sensitized subgroup in −D mice was markedly lower than that in normal mice (p=0.02), and that in +D mice (p<0.001). These results provide additional evidence that vitamin D deficiency impairs cell-mediated immunity in mice. The difference in SI between DNFB-sensitized subgroups in −D and −D+D mice was not significant (P>0.3).

The results obtained from the second experiment showed that the differences in thymus lymphocyte number between control subgroups and between DNFB-sensitized subgroups in −D+P and in +D+P groups were not significant (P>0.3 and >0.05, respectively; not shown). There were also no significant differences in stimulation index between control subgroups and between DNFB-sensitized subgroups in −D+P and +D+P groups (P>0.9 and >0.6, respectively; not shown).

DISCUSSION

The development of a truly vitamin D-deficient mouse model provided the tool for an investigation of the role of vitamin D in immunity. It is difficult, if not impossible, to attain true vitamin D-deficiency in mice by feeding a vitamin D deficient diet to commercially available mice. Usually vitamin D deficiency is verified by determining serum concentrations of 25-OH–$D_3$ and calcium. Of course, serum 1,25-$(OH)_2D_3$ concentration is also an important index to assess whether the animals are vitamin D deficient, but the amount of blood available from mice prohibits assaying 1,25-$(OH)_2D_3$ levels by currently available methods. Thus, one is forced to rely on serum 25-OH–D concentration together with serum calcium levels to verify vitamin D deficiency. With commercially available mice fed a purified −D diet containing 0.47% calcium, a lowered 25-OH–D level could be achieved; however, serum calcium level was no different from that of +D mice (unpublished observations). Therefore, it is clear that serum calcium concentration is a more sensitive index of vitamin D deficiency in mice. Allen (1984) J. Nutr. 114, 42–49 has reported that plasma total calcium levels in vitamin D-deficient lactating mice fed −D diet with 3% calcium were not significantly different from the levels in the control mice fed the +D diet, though the difference of serum 25 OH–D levels between both groups were significant. In order to achieve true vitamin D deficiency in mice, pregnant mothers must be fed a −D diet immediately after conception and their pups maintained on the deficient diet. Continual depletion is necessary including purified vitamin D-free diets and an absence of ultraviolet light.

Delayed-type hypersensitivity of skin contact reaction is a classical test of cell-mediated immunity. Robinson and Naysmith (1975) Scand. J. Immunol. 5, 299–304 assessed the merits of four different methods for measuring DTH reaction to protein antigen in mice: increase in thickness of the footpad, or ear; arrival of 51 Cr-labeled syngeneic lymph node cells at the challenge site in the ear, and accumulation of $^{125}$I-labeled 5-iododeoxyuridin (IUdR) at the challenge site in the ear. Direct measurement of an increase in ear thickness following challenge gave the most sensitive and consistent results and offers a reliable method. To avoid effect of choice of position during measurement of ear thickness and effect of pressure in the ourse of measuring ear thickness, we also used $^3$H-thymidine incorporation into the ears. This method is based on the assumption that cells proliferating in response to antigen incorporate $^3$H-thymidine as a permanent label.

Proliferation of mononuclear cells or lymphocytes obtained from organs has also been used to assess cell-mediated immunity. Tabata, Suzuki, Kikunami, Matsushita, Inoue, Okamoto, Miki, Nishizawa, and Morii (1986) J. Clin. Endocrinol. Metab. 63, 1218–1221 observed directly cell proliferation responses to mitogen PHA and PWM (pokeweed mitogen) as measured by $^3$H-thymidine uptake and used stimulation index of peripheral blood mononuclear cells to assess the effect of 1α-hydroxyvitamin $D_3$ [1α-OH–D] on cell-mediated immunity in hemodialyzed patients. In the present experiments, the stimulation index in thymus lymphocytes was measured to assess the effect of vitamin D deficiency on cell-mediated immunity. No significant differences in thymus lymphocyte number or of SI of the thymus lymphocytes between the nonsensitized −D group and +D group (or in normal group) was found. However, in sensitized mice thymus lymphocytes from −D mice gave lower stimulation index than those from the +D (or normal) mice. Provvedini, Rulot, Sobol, Tsoukas and Manolagas, (1987) J. Bone Min. Res. 2, 239–247 found that thymus lymphocytes in the early stages of activation possess in vivo, the 1,25-$(OH)_2D_3$ receptor protein appears and suggested that 1,25-$(OH)_2D_3$ may act in vivo on these cells. A positive correlation between 1,25-$(OH)_2D_3$ binding and the activation phase of thymus lymphocytes have been detected (Provvedini, Rulot, Sobol, Tsoukas and Manolagas, (1987) J. Bone Min. Res. 2, 239–247). The 1,25-(OH)$_2$D$_3$ receptors in bovine and mouse immature thymic lymphocytes also have been found (Reinhardt, Horst, Littledike, and Beitz, (1982) Biochem. Biophys. Res. Commun. 106, 1012–1018 and David, Koren, Novogrodsky, and Liberman, (1984) Biochem. Biophys. Res. Commun. 123, 163–169). Orally administered 1α-OH-D$_3$ prevents thymic involution in rats with renal osteodystrophy (Ohsugi, Nakano, Komori, Ueno, Sugawara, Fukushima, Yamamoto, Nishi, Masuda, and Matsuno, (1985) in "Vitamin D Chemical, Biochemical and Clinical Update." (Normal, Schaefer, Grigoleit, and Herrath, Eds.), p. 209–218, DeGruyter, Berlin, N.Y.). It appears clear that the absence of 1,25-(OH)$_2$D$_3$ impairs T-lymphocyte proliferation.

Some authors (Ohsugi, et al supra; Zarrabeitia, Riancho, Francisco, and Gonzalez-Macias, (1990) Nephron 55, 110–113; Harwick, Kalmanson, and Guze, (1978) Nephron 23, 293–296; Touraine, Revillard, Brochilherd, and Traeger, (1975) Nephron 14, 195–208; Kauffman, Manzler, and Phair, (1975) Clin. Exp. Immunol. 22, 54–61; Nakhla, and Goggin, (1973) Immunology 24, 229–235; Selroos, Pasternack, and Virolainen, (1973) Clin. Exp. Immunol. 14, 365–370; and Rickers, Christiansen, Christiansen, Christiansen, and Rodbro, (1985) Nephron 39, 267–271) have demonstrated that chronic renal failure in humans results in impaired cell-mediated immunity. Serum 1,25-(OH)$_2$D$_3$ levels are decreased in hemodialyzed and nonhemodialyzed renal failure patients (Selroos, et al, supra 1α-hydroxyvitamin D$_3$ has therapeutic value in the management of the patients, and can restore cell-mediated immunity (Tabata, et al, supra; and Ogushi, et al supra. A positive correlation between 1,25-(OH)$_2$D$_3$ concentration and Tuberculin test (PPD), a measured index of delayed-type hypersensitivity response in renal failure patients, has been reported (Lind, Wengle, Sorensen, and Ljunghall, (1990) Exp. Clin. Endocrinol. 95, 271–274). Thus, the absence of 1,25-(OH)$_2$D$_3$ in these circumstances could well be responsible for these findings.

The in vitro and clinical results suggest a discrepancy: vitamin D metabolites possess an immunoinhibitory effect in vitro, but a stimulatory effect in vivo. Most of the experiments in vitro have been performed with 1,25-(OH)$_2$D$_3$ in excess of its physiological concentration. Zarrabeitia et al., supra, demonstrated that the addition of 1,25-(OH)$_2$D$_3$ at concentrations in the physiological range ($10^{-11}$ M) induced a small, but marginally significant (11%), increase in the proliferation of lymphocytes from hemodialysis patients; superphysiological concentration ($10^{-9}$–$10^{-7}$M) induced a marked inhibition (up to 60% of control values) of mitosis in cells from both in patients and in healthy subjects. It is obvious that all these results cannot be explained by the present in vivo findings. However, the high concentrations of 1,25-(OH)$_2$D$_3$ in vitro may not be achieved in vivo.

It is clear that a deficiency of vitamin D causes an impaired cell-mediated immune response in vivo. In addition, it is of some interest that vitamin D administration for 3 weeks cannot restore normal cell-mediated immunity in vitamin D-deficient mice, though serum calcium and 25-OH-D can be restored to normal levels in these animals. It is possible that prolonged deficiency of vitamin D may cause developmental defects in the immune system that cannot be quickly repaired upon later administration of vitamin D. The results reported herein suggest that a more prolonged exposure to vitamin D is required to restore the cell-mediated immunity in mice.

TABLE 1

Purified diet for mice

| Component | % by weight | | |
|---|---|---|---|
| Cerelose | 64.4 | | |
| Casein | 18.0 | | |
| Cystine | 0.2 | | |
| Calcium carbonate (CaCO$_3$) | 1.11 | | |
| Celluflour | 3.0 | | |
| Choline chloride | 0.2 | | |
| Equimolar phosphates[1] | 0.9 | | |
| Salt mixture[2] | 2.0 | | |
| KCl | 57.7 | ZnSO$_4$.7H$_2$O | 0.44 |
| NaCl | 20.9 | (NH$_4$) 6Mo$_7$O$_{24}$.4H$_2$O | 0.005 |
| MgSO$_4$ | 17.9 | FeSO$_4$.7H$_2$O | 3.22 |
| NaF | 0.113 | CuSO$_4$.5H$_2$O | 0.78 |
| KI | 0.01 | MnSO$_4$.H$_2$O | 0.04 |
| | | CoCl$_2$.6H$_2$O | 0.004 |
| Water soluble vitamin mixture[2] | 0.2 | | |
| Thiamin (B1) | 0.5 | | |
| Riboflavin (B2) | 0.5 | | |
| Pyridoxine (B6) | 0.5 | | |
| Calcium pantothenate | 2.8 | | |
| Nicotinamide | 2.0 | | |
| Inositol | 20.0 | | |
| Folic acid | 0.02 | | |
| Vitamin B12 (cynnacobotin) | 0.002 | | |
| Biotin | 0.01 | | |
| Cerelose (Glucose monohydrate) | 73.7 | | |
| Wesson oil | 10.0 | | |

[1]KH$_2$PO$_4$/K$_2$HPO$_4$ = 408.3/522.5 (W/W)
[2]The component of this mixture is % by weight of this mixture itself.

TABLE 2

Components of fat-soluble vitamin solution

| Vitamin | g/l of Wesson oil | Amount/Kg of dry diet |
|---|---|---|
| Vitamin A (β-carotene) | 0.4 | 6667 IU (2mg) |
| Vitamin D[2] (ergocalciferol)[1] | 0.02535 | 5070 IU (126.75 μg) |
| Vitamin E (di-tocopherol) | 5.0 | 25 IU (25 mg) |
| Vitamin K (menadione) | 0.6 | 3 mg |

[1]For + D diet only.

The most important finding is that vitamin D$_3$ is able to improve or restore an immune deficiency in mammals within about 3 weeks. Thus, deficiency of vitamin D in mammals does not produce irreversible suppression of immunity in vivo unlike vitamin A deficiency. These results also support the idea that vitamin D$_3$ is directly involved and plays an important role in cell mediated immunity in vivo.

Based on the above studies and findings, it has been determined that a vitamin D compound may be utilized to treat immunodeficiencies categorized as either acquired immunodeficiencies or inherited immunodeficiencies. Acquired immunodeficiencies include human immunodeficiency virus-I (HIV-1) infection, Herpes virus infections, Epstein-Barr virus infections, lepromatous leprosy, and diminished immune capacity resulting from skin bums in bum patients, i.e. burn related immunodeficiency. Inherited immunodeficiencies include adenosine deaminase deficiency (ADA SCID), purine nucleotide phosphorylase deficiency (PNP SCID), severe combined immune deficiency (IL-2 receptor deficiency, i.e. X LINKED SCID), DiGeorge syndrome (no thymus), partial DiGeorge syndrome (thymic aplasia) and Bare lymphocyte syndrome (no MHC class I or II molecules to mediate positive selection of T cells in the thymus).

The results of the vitamin D deficiency model presented herein also support the use of vitamin D compounds to treat specific T-cell immunodeficiencies. These T-cell immunodeficiencies include leucocyte adhesion deficiency, lazy-leucocyte syndrome, reticular dysgenesis, and Wiskott-Alrich syndrome (WAS).

What is claimed is:

1. A method for treating a T-cell immunodeficiency in a renal failure patient to increase an immune response in said mammal which comprises administering to said patient an amount of a vitamin D compound sufficient to improve the immunity of said patient, said T-cell immunodeficiency selected from the group consisting of leucocyte adhesion deficiency, lazy-leucocyte syndrome, reticular dysgenesis, and Wiscott-Aldrich syndrome.

2. The method of claim 1 wherein said T-cell immunodeficiency of said patient resulted from a vitamin D deficiency in said patient.

3. The method of claim 1 wherein said vitamin D compound is selected from a compound having the formula where $R^6$ and $R^7$ each represent hydrogen or taken together $R^6$ and $R^7$ represent a methylene group, $R^8$ represents hydrogen, hydroxy, or a protected- hydroxy, and where R is represented by the structure where the stereochemical center at carbon 20 in the side chain may have the R or S configuration, and where Z is selected from the group consisting of Y, —OY, —CH$_2$OY, —C≡CY and —CH=CHY, where the double bond may have the cis or trans stereochemical configuration, and where Y is selected from the group consisting of hydrogen, methyl, —CR$^5$O and a radical of the structure where m and n, independently, represent the integers from 0 to 5, where $R^1$ is selected from the group consisting of hydrogen, hydroxy, protected hydroxy, fluoro, trifluoromethyl, and $C_{1-5}$-alkyl, which may be straight chain or branched, and optionally, bear a hydroxy or protected-hydroxy substituent, and where each of $R^2$, $R^3$, and $R^4$, independently, is selected from the group consisting of hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =CR$^2$R$^3$, or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected hydroxy, or $C_{1-5}$ alkyl.

4. The method of claim 1 wherein said vitamin D compound is administered in an amount of from about 0.1 micrograms to about 2 milligrams per dose depending upon the vitamin D compound administered.

5. The method of claim 1 wherein said vitamin D compound is administered to said patient for about 3 weeks to about 8 months.

6. The method of claim 1 wherein said vitamin D compound is administered orally in a liquid vehicle ingestible by and non-toxic to said patient.

7. The method of claim 1 wherein said vitamin D compound is combined with a non-toxic pharmaceutically acceptable carrier prior to administration.

8. The method of claim 1 wherein said vitamin D compound used is vitamin D$_3$.

9. The method of claim 1 wherein said vitamin D compound used is 1α,25-dihydroxyvitamin D$_3$.

10. The method of claim 1 wherein said vitamin D compound used is 1α-hydroxyvitamin D$_3$.

11. The method of claim 1 wherein said vitamin D compound is administered intravenously.

12. A method for increasing an immune response in a patient with chronic renal failure having an immune deficiency which comprises administering to said patient an amount of 1α,25-dihydroxyvitamin D$_3$ sufficient to improve the immunity of said patient.

13. The method of claim 12 wherein said 1α,25-dihydroxyvitamin D$_3$ is administered in an amount of from about 0.1 micrograms to about 2 micrograms per dose.

14. The method of claim 12 wherein said 1α,25-dihydroxyvitamin D$_3$ is administered to said patient for about 3 weeks to about 8 months.

15. The method of claim 12 wherein said 1α,25-dihydroxyvitamin D$_3$ is administered intravenously.

16. The method of claim 12 wherein said 1α,25-dihydroxyvitamin D$_3$ is administered orally in a liquid vehicle ingestible by and non-toxic to said patient.

17. The method of claim 12 wherein said 1α,25-dihydroxyvitamin D$_3$ is combined with a non-toxic pharmaceutically acceptable carrier prior to administration.

* * * * *